United States Patent [19]

Hsu

[11] Patent Number: 4,990,525
[45] Date of Patent: Feb. 5, 1991

[54] SYNERGISTIC MICROBICIDAL COMBINATIONS CONTAINING 3-ISOTHIAZOLONE AND COMMERICAL BIOCIDES

[75] Inventor: Jemin C. Hsu, Fort Washington, Pa.

[73] Assignee: Rohm and Haas Company, Philadelphia, Pa.

[21] Appl. No.: 444,571

[22] Filed: Dec. 1, 1990

Related U.S. Application Data

[62] Division of Ser. No. 289,066, Dec. 22, 1988, Pat. No. 4,906,651.

[51] Int. Cl.$^5$ .................. A01N 43/32; A01N 43/80
[52] U.S. Cl. .......................... 514/372; 71/67; 514/452
[58] Field of Search .............. 514/372, 452; 71/67

[56] References Cited

U.S. PATENT DOCUMENTS

| | | | |
|---|---|---|---|
| 3,761,488 | 9/1973 | Lewis et al. | 260/302 |
| 4,105,431 | 8/1978 | Lewis et al. | 71/67 |
| 4,252,694 | 2/1981 | Lewis et al. | 252/545 |
| 4,265,899 | 5/1981 | Lewis et al. | 424/270 |
| 4,279,762 | 7/1981 | Lewis et al. | 252/475 |

OTHER PUBLICATIONS

Hueck, et al., Applied Microbial, vol. 14, No. 3, (1966), pp. 308–310, 314 and 319.
Schuster, C. A., vol. 105, (1986), 105:48812e.

*Primary Examiner*—Allen J. Robinson
*Attorney, Agent, or Firm*—Michael B. Fein

[57] ABSTRACT

This invention relates to synergistic antimicrobial and biocidal compositions comprising 5-chloro-2-methyl-4-isothiazolin-3-one and 2-methyl-4-isothiazolin-3-one and one or more commercial biocides for more effective, and broader control of microorganisms in various industrial systems.

5 Claims, No Drawings ically a mixture of 5-chloro-2-methyl-4-isothiazolin-3-one and 2-methyl-4-isothiazolin-3-one, is very effective against bacteria, fungi, and algae. The suggested dosages, sometimes, cannot achieve the best results for the control of microorganisms due to interfering nucleophiles, or due to less sensitive organisms in certain systems. To control the situations like these will need higher concentration of active ingredient which becomes more costly in the treatment. Therefore, the search for more effective and broader control methods to achieve the best results has continued. -->

SYNERGISTIC MICROBICIDAL COMBINATIONS CONTAINING 3-ISOTHIAZOLONE AND COMMERICAL BIOCIDES

This is a divisional of application Ser. No. 289,066, filed Dec. 22, 1988, now U.S. Pat. No. 4,906,651

BACKGROUND OF THE INVENTION

1. Field of the Invention

This invention relates to synergistic biocidal combinations including an isothiazolone and one or more of many commercial biocides for more effective and broader control of micro-organisms in various industrial systems. In particular, the present invention relates to the use of a mixture of 5-chloro-2-methyl-4-isothiazolin-3-one and 2-methyl-4-isothiazolin-3-one (also known as 5-chloro-2-methyl-3-isothiazolone and 2-methyl-3-isothiazolone, respectively) with one or more of the following 14 compounds: Hexahydro-1,3,5-triethyl-5-triazine; 5-bromo-5-nitro-1,3-dioxane; 2-(hydroxymethyl) aminoethanol; 2-(hydroxymethyl)amino-2methylpropanol α-benozyl-α-chloroformaldoxime; benzylbromoacetate; p-chloro-m-xylenol; bis-(2-hydroxy-5-chlorophenyl) sulfide; p-tolyldiiodomethylsulfone; 3-iodo-2-propynylbutylcarbamate; bis-(2-hydroxy-5-chlorophenyl)methylene; dipropylamine ether; dodecylamine; and 1-(3-chloroallyl)-3,5,7-triaza-1-azoniaadamantane chloride.

2. Prior Art

The isothiazolones are described in U.S. Pat. Nos. 3,761,488; 4,105,431; 4,252,694; 4,265,899 and 4,279,762. An excellent antimicrobial agent is a mixture of 75% 5-chloro-2-methyl-4-isothiazolin-3-one and 25% 2-methyl-4-isothiazolin-3-one, which is very effective against bacteria, fungi, and algae. The suggested dosages, sometimes, cannot achieve the best results for the control of microorganisms due to interfering nucleophiles, or due to less sensitive organisms in certain systems. To control the situations like these will need higher concentration of active ingredient which becomes more costly in the treatment. Therefore, the search for more effective and broader control methods to achieve the best results has continued.

Many other broad classes of biocidal agents are known. They are commercially available for the control of microorganisms in certain sections of various industrial systems such as paints, wood, textile, paper, pulp, leather, fur, tobacco, rope, plastics, fuel, oil, cosmetics, rubber, adhesives, latex emulsions, joint cements, water treatment, laundry, and metalworking industries, and the like. In general, high dosage requirements make them disadvantageous because of high treatment cost and interference with the formulation of finished product or the operation of the system. Sometimes many biocides cannot provide satisfactory performances even at high use concentrations due to weak activity against certain bacteria or fungi. Without effective control, loss of product, inferior product, production-time loss, health hazard, and other types of problems may occur in the systems.

It has been discovered that combinations of a mixture of 5-chloro-2-methyl-4-isothiazolin-3-one and 2-methyl-4-isothiazolin-3-one with one or more of the 14 compounds within a specified range of ratios results in synergistic biocidal activities against a wide range of microorganisms. The synergy in which the disruptive interaction on the organisms by the two compounds together is greater than the sum of both compounds taken alone does not arise from the expected activity of the components or from the expected improvement in activity. The synergistic combinations provide more effective and broader control of microorganisms in a number of industrial systems.

It is the principal object of this invention to provide the use of synergistic compositions which overcome the disadvantages of the prior art biocidal compositions.

Important applications of the synergistic antimicrobial compositions of the present invention include but are not limited to: inhibiting the growth of bacteria and fungi in aqueous and organic paints, adhesives, latex emulsions, and joint cements; preserving wood; preserving cutting fluids, controlling slime-producing bacteria and fungi in pulp and papermills and cooling towers; as a spray or dip treatment for textiles and leather to prevent mold growth; protecting paint films, especially exterior paints from attack by fungi which occurs during weathering of the paint film; protecting processing equipment from slime deposits during manufacture of cane and beet sugar; preventing microorganism buildup and deposits in air washer or scrubber systems and in industrial fresh water supply systems; controlling micro-organisms contamination and deposits in oil field drilling fluids and muds, and in secondary petroleum recovery processes; preventing bacterial and fungal growth in paper coating processes; controlling bacterial and fungal growth and deposits during the manufacture of various specialty boards, e.g., cardboard and particle board; preventing sap stain discoloration on freshly cut wood of various kinds; controlling bacterial fungal growth in clay and pigment slurries of various types; as a hard surface disinfectant to prevent growth of bacteria and fungi on walls, floors, etc.; in swimming pools to prevent algae growth; inhibiting the growth of harmful bacteria, yeasts, fungi on plants, trees, fruits, seeds, or soil; protecting animal dip compositions against the buildup of microorganisms, and in photoprocessing to prevent buildup of microorganisms, and the like.

The synergistic compositions of this invention may be added separately to an industrial system or may be formulated as a simple mixture comprising its essential ingredients, or together with a suitable carrier or solvent, or as an aqueous emulsion or dispersion.

SUMMARY OF THE INVENTION

Microbicidal compositions comprising a synergistic mixture the first component being a 3:1 ratio of 5-chloro-2-methyl-4-isothiazolin-3-one and 2-methyl-4isothiazolin-3-one (Compound A) and the second component which is one or more of the following compounds (Compound B) wherein the range of ratios of Compound A to Compound B (A:B) is from 8:1 to 1:200 exhibit synergistic biocidal and antimicrobial activity agains a wide range of microorganisms. More particularly, the invention relates to the use of a mixture of 5-chloro-2-methyl-4-isothiazolin-3-one and 2-methyl-4-isothiazolin-3-one in combination with one or more of the following 14 compounds: Hexahydro-1,3,5-triethyl-5-triazine; 5-bromo-5-nitro-1,3-dioxane; 2-(hydroxymethyl)amino-ethanol; 2-(hydroxymethyl)amino-2-methylpropanol; α-benzoyl-α-chloroformaldoxime; benzylbromoacetate; p-chloro -m-xylenol; bis-(2-hydroxy-5-chlorophenyl)sulfide; p-tolyldiiodomethylsulfone; 3-iodo-2-propynylbutylcarbamate; bis-(2-hydroxy-5-chlorophenyl)methylene; dipropylamine ether; dodecylamine; and 1-(3-chloroallyl)-3,5,7-triaza-1-azoniaadamantane chloride.

The invention also relates to a method of inhibiting the growth of bacteria, fungi or algae in a locus subject to contamination by bacteria, fungi or algae, which comprises incorporating into or onto the locus in an amount which is effective to adversely affect the growth of bacteria, fungi or algae one or more of the synergistic combinations described above.

The composition of the invention can be formulated as a solution in water. While the amount of the instant composition in the formulated solution can vary over a wide range, the solutions can conveniently be formulated to contain from about 5 to about 100 ppm of the composition in solution, with the preferred range being from about 10 to 50 ppm of the composition. In formulating the solutions, other solvents which are water-miscible, such as ethyl alcohol, propyl alcohol, isopropyl alcohol, diethylene glycol, dipropylene glycol, polyethylene glycol, diethylene glycol ethyl ether, and the like, may be employed in order to aid in solubilizing the active components. Furthermore, various other conventional additives may be employed, such as surfactants, dispersing agents, corrosion inhibitors, and the like.

In general, the ratio of the first component to second component is in the range of from about 8:1 to 1:200. The other ratios are given in the examples.

GENERAL DESCRIPTION OF THE PREFERRED EMBODIMENT

The synergistic combinations have a wide range of applications, including all areas where the individual biocides and preservatives are currently employed. In addition, the synergistic combinations can be used beyond their original intended uses because of the newly-acquired, more effective, broader spectrum of activities.

The synergism of these two-component combinations is demonstrated by testing a wide range of concentrations and ratios of compounds, generated by two-fold serial dilutions in a liquid growth medium of a biocide in one dimension and another biocide in the second dimension, against a bacterium *Escherichia coli* (ATCC 11229) or a fungus *Candida albicans* (ATCC 11651), or a mixed culture of bacteria and fungi which are natural contaminants of a metalworking fluid, or a more tolerant pseudomonad isolated from a surfactant. Each test tube was inoculated to about $2 \times 10^7$ bacteria per ml or $2 \times 10^6$ fungi per ml. The lowest concentrations of each compound or mixtures to inhibit visible growth (turbidity) at 37° for *E. coli* and at 30° C. for the pseudomonad, *C. albicans*, or the mixed culture for over 2 days is the minimum inhibitory concentration (MIC). The lowest concetration of each compound or the mixtures to kill 99.99% of fungi or 99.999% of bacteria after certain periods of exposure from 1 day to 7 days is taken as minimum biocidal concentration (MBC). Both MIC and MBC are taken as end points of activity. End points for the mixtures of compound A and compound B were then compared with the end points for compound A alone and compound B alone. Synergism was determined by an industrially accepted method described by Kull, F.C.; Eisman, P.C.; Sylwestrowicz, H.D. and Mayer, R.L., in applied Microbiology 9:538–541 (1961) using the ratio determined by $$\frac{Qa}{QA} + \frac{Qb}{QB} = \text{Synergy Index (SI)}$$

wherein

QA = concentration of compound A in parts per million (ppm), acting alone, which produced an end point.

Qa = concentration of compound A in ppm, in the mixture, which produced an end point.

QB = concentration of compound B in ppm, acting lone, which produced an end point.

Qb = concentration of compound B in ppm, in the mixture, which produced an end point when the sum of Qa/QA and Qb/QB is greater than one, antagonism is indicated. When the sum is equal to one additivity is indicated, and when less than one synergism is demonstrated.

The test results for demonstration of synergism of biocide combinations are shown in Table 1 through Table 14. Each table is organized to show:

1. the specific combination of compound A and compound B;
2. test against *E. coli* (Ecol) or *C. albicans* (Calb), or a pseudomonad species (P. sp), or a mixed culture of bacteria and fungi (mixed);
3. test medium by either trypticase soy broth (TSB) or a minimal salt medium +0.2% glucose (M9G);
4. the method of evaluation (test) by either MIC or MBC. The MBC1d means MBC determined after 1-day exposure to biocides. MBC2d means MBC determined after 2-days exposure to biocides, etc.;
5. the end-point activity in ppm measured by MIC or MBC for compound A alone (QA), for compound B alone (QB), for compound A in the mixture (Qa), or for compound B in the mixture (Qb);
6. the calculation for synergy index (SI) based on the formula SI=Qa/QA+Qb/QB, and for the ratio of compound A to compound B in the synergistic combinations (Qa:Qb);
7. the range of ratios for synergism and the preferred ratios.

TABLE 1

Combination of 5-chloro-2-methyl-4-isothiazolin-3-one and 2-methyl-4-isothiazolin-3-one (Compound A) and hexahydro-1,3,5-triethyl-s-triazine (Compound B)

| Microbe | Media | Test | QA | QB | Qa | Qb | Qa/QA | Qb/QB | SI |
|---|---|---|---|---|---|---|---|---|---|
| Ecol | TSB | MIC | 2.5 | 250.0 | 1.3 | 62.0 | 0.50 | 0.25 | 0.75 |
| | | MBC2d | 5.0 | 1000.0 | 0.6 | 250.0 | 0.12 | 0.25 | 0.37 |
| | | | 5.0 | 1000.0 | 2.5 | 8.0 | 0.50 | 0.01 | 0.51 |
| | | MBC6d | 5.0 | 500.0 | 0.6 | 250.0 | 0.12 | 0.50 | 0.62 |
| | | | 5.0 | 500.0 | 1.3 | 125.0 | 0.25 | 0.25 | 0.50 |
| | | | 5.0 | 500.0 | 2.5 | 4.0 | 0.50 | 0.01 | 0.51 |
| Calb | TSB | MIC | 1.3 | 1000.0 | 0.3 | 500.0 | 0.25 | 0.50 | 0.75 |
| | | | 1.3 | 1000.0 | 0.6 | 250.0 | 0.50 | 0.25 | 0.75 |

TABLE 1-continued

Combination of 5-chloro-2-methyl-4-isothiazolin-3-one and 2-methyl-4-isothiazolin-3-one (Compound A) and hexahydro-1,3,5-triethyl-s-triazine (Compound B)

| Microbe | Media | Test | QA | QB | Qa | Qb | Qa/QA | Qb/QB | SI |
|---|---|---|---|---|---|---|---|---|---|
| | | MBC2d | 1.3 | 1000.0 | 0.3 | 500.0 | 0.25 | 0.50 | 0.75 |
| | | | 1.3 | 1000.0 | 0.6 | 250.0 | 0.50 | 0.25 | 0.75 |
| | | MBC6d | 1.3 | 1000.0 | 0.3 | 500.0 | 0.25 | 0.50 | 0.75 |
| | | | 1.3 | 1000.0 | 0.6 | 250.0 | 0.50 | 0.25 | 0.75 |
| P.sp | TSB | MIC | 8.0 | 250.0 | 1.0 | 125.0 | 0.13 | 0.50 | 0.63 |
| | | | 8.0 | 250.0 | 2.0 | 62.0 | 0.25 | 0.25 | 0.50 |
| | | | 8.0 | 250.0 | 4.0 | 31.0 | 0.50 | 0.12 | 0.62 |
| | | MBC2d | 31.0 | 500.0 | 4.0 | 125.0 | 0.13 | 0.25 | 0.38 |
| | | | 31.0 | 500.0 | 8.0 | 62.0 | 0.26 | 0.12 | 0.38 |
| | | | 31.0 | 500.0 | 16.0 | 4.0 | 0.52 | 0.01 | 0.52 |
| | | MBC6d | 31.0 | 500.0 | 4.0 | 125.0 | 0.13 | 0.25 | 0.38 |
| | | | 31.0 | 500.0 | 8.0 | 62.0 | 0.26 | 0.12 | 0.38 |
| | | | 31.0 | 500.0 | 16.0 | 4.0 | 0.52 | 0.01 | 0.52 |
| Ecol | M9G | MIC | 0.6 | 31.0 | 0.3 | 2.0 | 0.50 | 0.06 | 0.56 |
| | | MBC1d | 0.6 | 31.0 | 0.3 | 2.0 | 0.50 | 0.06 | 0.56 |
| Mixed | TSB | MIC | 3.1 | 250.0 | 0.6 | 62.0 | 0.20 | 0.25 | 0.45 |
| | | MBC1d | 25.0 | 1000.0 | 2.5 | 250.0 | 0.10 | 0.25 | 0.35 |
| | | MBC4d | 3.1 | 250.0 | 0.6 | 62.0 | 0.20 | 0.25 | 0.45 |

The synergistic ratios of compound A:compound B range from 4:1 to 1:1600. The preferred ratios are 4:1 to 1:100.

TABLE 2

Combination of Compound A and 5-Bromo-5-nitro-1,3-dioxane (Compound B)

| Microbe | Media | Test | QA | QB | Qa | Qb | Qa/QA | Qb/QB | SI |
|---|---|---|---|---|---|---|---|---|---|
| Ecol | TSB | MIC | 2.5 | 250.0 | 0.6 | 125.0 | 0.25 | 0.50 | 0.75 |
| | | | 2.5 | 250.0 | 1.3 | 31.0 | 0.50 | 0.12 | 0.62 |
| | | MBC2d | 5.0 | 250.0 | 1.3 | 125.0 | 0.25 | 0.50 | 0.75 |
| | | MBC6d | 5.0 | 250.0 | 1.3 | 62.0 | 0.25 | 0.25 | 0.50 |
| | | | 5.0 | 250.0 | 2.5 | 8.0 | 0.50 | 0.03 | 0.53 |
| Calb | TSB | MIC | 1.3 | 250.0 | 0.3 | 125.0 | 0.25 | 0.50 | 0.75 |
| | | | 1.3 | 250.0 | 0.6 | 62.0 | 0.50 | 0.25 | 0.74 |
| | | MBC2d | 1.3 | 500.0 | 0.1 | 250.0 | 0.06 | 0.50 | 0.56 |
| | | | 1.3 | 500.0 | 0.6 | 62.0 | 0.50 | 0.12 | 0.62 |
| | | MBC6d | 2.5 | 500.0 | 0.2 | 250.0 | 0.06 | 0.50 | 0.56 |
| | | | 2.5 | 500.0 | 0.6 | 62.0 | 0.25 | 0.12 | 0.37 |
| | | | 2.5 | 500.0 | 1.3 | 2.0 | 0.50 | 0.00 | 0.50 |
| P.sp | TSB | MIC | 16.0 | 500.0 | 1.0 | 250.0 | 0.06 | 0.50 | 0.56 |
| | | | 16.0 | 500.0 | 8.0 | 125.0 | 0.50 | 0.25 | 0.75 |
| | | MBC2d | 31.0 | 1000.0 | 1.0 | 500.0 | 0.03 | 0.50 | 0.53 |
| | | | 31.0 | 1000.0 | 16.0 | 125.0 | 0.52 | 0.13 | 0.64 |
| | | MBC6d | 31.0 | 1000.0 | 1.0 | 500.0 | 0.03 | 0.50 | 0.53 |
| | | | 31.0 | 1000.0 | 16.0 | 250.0 | 0.52 | 0.25 | 0.77 |
| Ecol | M9G | MIC | 0.6 | 62.0 | 0.3 | 16.0 | 0.50 | 0.26 | 0.76 |
| | | | 0.6 | 62.0 | 0.2 | 31.0 | 0.26 | 0.50 | 0.76 |
| | | MBC1d | 0.6 | 62.0 | 0.3 | 16.0 | 0.50 | 0.26 | 0.76 |
| | | | 0.6 | 62.0 | 0.2 | 31.0 | 0.26 | 0.50 | 0.76 |
| Mixed | TSB | MIC | 3.1 | 125.0 | 0.3 | 16.0 | 0.10 | 0.13 | 0.23 |
| | | MBC4d | 3.1 | 250.0 | 1.3 | 62.0 | 0.40 | 0.25 | 0.65 |

The synergistic ratios of compound A:compound B range from 6.5:1 to 1:250. The preferred ratios are 6.5:1 to 1:125

TABLE 3

Combination of Compound A and 2-(Hydroxymethyl)aminoethanol (Compound B)

| Microbe | Media | Test | QA | QB | Qa | Qb | Qa/QA | Qb/QB | SI |
|---|---|---|---|---|---|---|---|---|---|
| Ecol | TSB | MIC | 5.0 | 1000.0 | 0.6 | 500.0 | 0.12 | 0.50 | 0.62 |
| | | | 5.0 | 1000.0 | 1.3 | 250.0 | 0.25 | 0.25 | 0.50 |
| | | | 5.0 | 1000.0 | 2.5 | 16.0 | 0.50 | 0.02 | 0.52 |
| | | MBC2d | 5.0 | 1000.0 | 1.3 | 250.0 | 0.25 | 0.25 | 0.50 |
| | | | 5.0 | 1000.0 | 2.5 | 62.0 | 0.50 | 0.06 | 0.56 |
| | | MBC6d | 5.0 | 1000.0 | 1.3 | 500.0 | 0.25 | 0.50 | 0.75 |
| | | | 5.0 | 1000.0 | 2.5 | 125.0 | 0.50 | 0.13 | 0.63 |
| Calb | TSB | MIC | 2.5 | 1000.0 | 1.3 | 16.0 | 0.50 | 0.02 | 0.52 |
| | | MBC2d | 2.5 | 1000.0 | 0.6 | 125.0 | 0.25 | 0.13 | 0.37 |
| | | MBC6d | 2.5 | 1000.0 | 1.3 | 16.0 | 0.50 | 0.02 | 0.52 |
| P.sp | TSB | MIC | 16.0 | 1000.0 | 1.0 | 500.0 | 0.06 | 0.50 | 0.56 |

TABLE 3-continued

Combination of Compound A and 2-(Hydroxymethyl)aminoethanol (Compound B)

| Microbe | Media | Test | QA | QB | Qa | Qb | Qa/QA | Qb/QB | SI |
|---|---|---|---|---|---|---|---|---|---|
| | | MBC2d | 31.0 | 1000.0 | 8.0 | 500.0 | 0.26 | 0.50 | 0.76 |
| | | MBC6d | 31.0 | 1000.0 | 16.0 | 500.0 | 0.50 | 0.50 | 1.00 |
| Ecol | M9G | MIC | 0.6 | 125.0 | 0.1 | 31.0 | 0.13 | 0.25 | 0.38 |
| | | | 0.6 | 125.0 | 0.1 | 62.0 | 0.08 | 0.50 | 0.58 |
| | | MBCld | 0.6 | 125.0 | 0.1 | 31.0 | 0.13 | 0.25 | 0.38 |
| | | | 0.6 | 125.0 | 0.1 | 62.0 | 0.08 | 0.50 | 0.58 |
| Mixed | TSB | MIC | 3.1 | 1000.0 | 0.3 | 62.0 | 0.10 | 0.06 | 0.16 |
| | | MBCld | 25.0 | 1000.0 | 0.3 | 62.0 | 0.01 | 0.06 | 0.07 |
| | | MBC4d | 3.1 | 1000.0 | 0.3 | 62.0 | 0.10 | 0.06 | 0.16 |

The synergistic ratios of compound A:compound B range from 1:62 to 1:1600. The preferred ratios are 1:25 to 1:200.

TABLE 4

Combination of Compound A and 2-(hydroxymethyl)aminio-2-methylpropanol (Compound B)

| Microbe | Media | Test | QA | QB | Qa | Qb | Qa/QA | Qb/QB | SI |
|---|---|---|---|---|---|---|---|---|---|
| Calb | TSB | MIC | 2.5 | 1000.0 | 1.3 | 500.0 | 0.50 | 0.50 | 1.00 |
| Ecol | M9G | MIC | 0.6 | 31.0 | 0.1 | 16.0 | 0.13 | 0.52 | 0.65 |
| | | MBCld | 0.6 | 250.0 | 0.3 | 31.0 | 0.50 | 0.12 | 0.62 |
| | | | 0.6 | 250.0 | 0.1 | 62.0 | 0.13 | 0.25 | 0.38 |
| Mixed | TSB | MIC | 3.1 | 1000.0 | 0.3 | 62.0 | 0.10 | 0.06 | 0.16 |
| | | MBCld | 25.0 | 1000.0 | 2.5 | 500.0 | 0.10 | 0.50 | 0.60 |
| | | MBC4d | 3.1 | 1000.0 | 0.6 | 125.0 | 0.20 | 0.13 | 0.33 |

The snyergistic ratios of compound A:compound B range from 1:100 to 1:800. The preferred ratios are 1:100 to 1:200.

TABLE 5

Combination of Compound A and α-Benzoyl-α-chloroformaldoxime (Compound B)

| Microbe | Media | Test | QA | QB | Qa | Qb | Qa/QA | Qb/QB | SI |
|---|---|---|---|---|---|---|---|---|---|
| Ecol | M9G | MIC | 0.2 | 250.0 | 0.02 | 31 | 0.13 | 0.12 | 0.25 |
| | | | 0.2 | 250.0 | 0.08 | 0.5 | 0.50 | 0.00 | 0.50 |
| | | MBC4d | 0.2 | 500.0 | 0.02 | 62.0 | 0.13 | 0.12 | 0.25 |
| | | | 0.2 | 500.0 | 0.04 | 31.0 | 0.25 | 0.06 | 0.31 |
| | | | 0.2 | 500.0 | 0.08 | 16.0 | 0.50 | 0.03 | 0.53 |
| | | MBC7d | 0.2 | 250.0 | 0.02 | 31.0 | 0.13 | 0.12 | 0.25 |
| | | | 0.2 | 250.0 | 0.08 | 0.5 | 0.50 | 0.00 | 0.50 |
| Calb | TSB | MIC | 1.3 | 2000.0 | 0.62 | 1000.0 | 0.50 | 0.50 | 1.00 |
| | | MBC2d | 1.3 | 2000.0 | 0.62 | 500.0 | 0.50 | 0.25 | 0.75 |
| P.sp | TSB | MIC | 4.0 | 1000.0 | 1.00 | 500.0 | 0.25 | 0.50 | 0.75 |
| | | | 4.0 | 1000.0 | 2.00 | 125.0 | 0.50 | 0.13 | 0.63 |
| | | MBC2d | 16.0 | 2000.0 | 1.00 | 500.0 | 0.06 | 0.25 | 0.31 |
| | | | 16.0 | 2000.0 | 4.00 | 125.0 | 0.25 | 0.06 | 0.31 |
| | | | 16.0 | 2000.0 | 8.0 | 16.0 | 0.50 | 0.01 | 0.51 |
| | | MBC6d | 16.0 | 2000.0 | 1.00 | 500.0 | 0.05 | 0.25 | 0.31 |
| | | | 16.0 | 2000.0 | 4.00 | 125.0 | 0.25 | 0.06 | 0.31 |
| | | | 16.0 | 2000.0 | 8.00 | 31.0 | 0.50 | 0.02 | 0.52 |
| Ecol | TSB | MIC | 1.3 | 2000.0 | 0.62 | 500.0 | 0.50 | 0.25 | 0.75 |
| | | MBCld | 1.3 | 2000.0 | 0.62 | 500.0 | 0.50 | 0.25 | 0.75 |

The synergistic ratios of compound A:compound B range from 1:2 to 1:3200. The preferred ratios are 1:4 to 1:31.

TABLE 6

Combination of Compound A and Benzyl bromoacetate (Compound B)

| Microbe | Media | Test | QA | QB | Qa | Qb | Qa/QA | Qb/QB | SI |
|---|---|---|---|---|---|---|---|---|---|
| Ecol | TSB | MIC | 0.6 | 62.0 | 0.3 | 16.0 | 0.50 | 0.26 | 0.76 |
| | | MBCld | 0.6 | 62.0 | 0.3 | 16.0 | 0.50 | 0.26 | 0.76 |
| Calb | TSB | MIC | 1.3 | 16.0 | 0.6 | 4.0 | 0.50 | 0.25 | 0.75 |
| | | MBCld | 1.3 | 16.0 | 0.3 | 8.0 | 0.25 | 0.50 | 0.75 |
| | | | 1.3 | 16.0 | 0.6 | 4.0 | 0.50 | 0.25 | 0.75 |
| | | MBC4d | 1.3 | 16.0 | 0.3 | 8.0 | 0.25 | 0.50 | 0.75 |
| | | | 1.3 | 16.0 | 0.6 | 4.0 | 0.50 | 0.25 | 0.75 |

TABLE 6-continued

Combination of Compound A and Benzyl bromoacetate (Compound B)

| Microbe | Media | Test | QA | QB | Qa | Qb | Qa/QA | Qb/QB | SI |
|---|---|---|---|---|---|---|---|---|---|
| Ecol | M9G | MIC | 0.3 | 62.0 | 0.2 | 8.0 | 0.52 | 0.13 | 0.65 |
|  |  |  | 0.3 | 62.0 | 0.1 | 16.0 | 0.16 | 0.26 | 0.42 |
|  |  | MBCld | 0.3 | 62.0 | 0.2 | 8.0 | 0.52 | 0.13 | 0.65 |
|  |  |  | 0.3 | 62.0 | 0.1 | 16.0 | 0.16 | 0.26 | 0.42 |
| Mixed | TSB | MIC | 3.1 | 100.0 | 0.6 | 8.0 | 0.20 | 0.08 | 0.28 |
|  |  | MBC4d | 3.1 | 100.0 | 1.3 | 16.0 | 0.40 | 0.16 | 0.56 |

The synergistic ratios of compound A:compound B range from 1:6.2 to 1:400. The preferred ratios are 1:6.2 to 1:50.

TABLE 7

Combination of Compound A and p-Chloro-m-xylenol (Compound B)

| Microbe | Media | Test | QA | QB | Qa | Qb | Qa/QA | Qb/QB | SI |
|---|---|---|---|---|---|---|---|---|---|
| Ecol | M9G | MIC | 0.3 | 250.0 | 0.16 | 0.3 | 0.52 | 0.00 | 0.52 |
|  |  |  | 0.3 | 250.0 | 0.02 | 125.0 | 0.06 | 0.50 | 0.56 |
|  |  | MBCld | 2.5 | 250.0 | 0.02 | 125.0 | 0.01 | 0.50 | 0.51 |
|  |  |  | 2.5 | 250.0 | 0.31 | 62.0 | 0.12 | 0.25 | 0.37 |
|  |  |  | 2.5 | 250.0 | 0.62 | 31.0 | 0.25 | 0.12 | 0.37 |
|  |  | MBC4d | 0.3 | 250.0 | 0.08 | 125.0 | 0.28 | 0.50 | 0.78 |
|  |  |  | 0.3 | 250.0 | 0.16 | 0.3 | 0.52 | 0.00 | 0.52 |
|  |  | MBC7d | 0.3 | 250.0 | 0.02 | 125.0 | 0.06 | 0.50 | 0.56 |
|  |  |  | 0.3 | 250.0 | 0.16 | 0.3 | 0.52 | 0.00 | 0.52 |
| Calb | TSB | MIC | 2.5 | 250.0 | 1.25 | 31.0 | 0.50 | 0.12 | 0.62 |
| Ecol | TSB | MIC | 0.6 | 125.0 | 0.16 | 62.0 | 0.26 | 0.50 | 0.75 |
|  |  | MBCld | 0.6 | 125.0 | 0.16 | 62.0 | 0.26 | 0.50 | 0.75 |
| Mixed | TSB | MIC | 3.1 | 125.0 | 0.31 | 62.0 | 0.10 | 0.50 | 0.60 |
|  |  | MBCld | 25.0 | 250.0 | 0.62 | 125.0 | 0.02 | 0.50 | 0.52 |
|  |  | MBC4d | 3.1 | 125.0 | 0.31 | 62.0 | 0.10 | 0.50 | 0.60 |

The synergistic ratios of compound A:compound B range from 1:1.6 to 1:6250. The preferred ratios are 1:1.6 to 1:200.

TABLE 8

Combination of Compound A and Bis-(2-hydroxy-5-chlorophenyl)sulfide (Compound A)

| Microbe | Media | Test | QA | QB | Qa | Qb | Qa/QA | Qb/QB | SI |
|---|---|---|---|---|---|---|---|---|---|
| Ecol | M9G | MIC | 0.6 | 31.0 | 0.2 | 8.0 | 0.26 | 0.26 | 0.52 |
|  |  |  | 0.6 | 31.0 | 0.1 | 16.0 | 0.13 | 0.52 | 0.65 |
|  |  |  | 0.6 | 31.0 | 0.2 | 8.0 | 0.26 | 0.26 | 0.52 |
|  |  |  | 0.6 | 31.0 | 0.1 | 16.0 | 0.13 | 0.52 | 0.65 |

The synergistic ratios of compound A:compound B range from 1:50 to 1:200. The preferred ratios are 1:50 to 1:200.

TABLE 9

Combination of Compound A and p-Tolyldiiodomethylsulfone (Compound B)

| Microbe | Media | Test | QA | QB | Qa | Qb | Qa/QA | Qb/QB | SI |
|---|---|---|---|---|---|---|---|---|---|
| Ecol | TSB | MIC | 5.0 | 62.0 | 0.6 | 31.0 | 0.12 | 0.50 | 0.62 |
|  |  |  | 5.0 | 62.0 | 1.3 | 8.0 | 0.25 | 0.13 | 0.38 |
|  |  |  | 5.0 | 62.0 | 2.5 | 0.1 | 0.50 | 0.00 | 0.50 |
|  |  | MBC2d | 5.0 | 62.0 | 0.6 | 31.0 | 0.12 | 0.50 | 0.62 |
|  |  |  | 5.0 | 62.0 | 1.3 | 8.0 | 0.25 | 0.13 | 0.38 |
|  |  | MBC6d | 5.0 | 62.0 | 0.6 | 31.0 | 0.12 | 0.50 | 0.62 |
|  |  |  | 5.0 | 62.0 | 1.3 | 8.0 | 0.25 | 0.13 | 0.38 |
|  |  |  | 5.0 | 62.0 | 2.5 | 4.0 | 0.50 | 0.06 | 0.56 |
| Calb | TSB | MIC | 1.3 | 2.0 | 0.1 | 1.0 | 0.06 | 0.50 | 0.56 |
|  |  |  | 1.3 | 2.0 | 0.6 | 0.5 | 0.50 | 0.25 | 0.75 |
|  |  | MBC2d | 1.3 | 2.0 | 0.2 | 1.0 | 0.13 | 0.50 | 0.63 |
|  |  |  | 1.3 | 2.0 | 0.6 | 0.5 | 0.50 | 0.25 | 0.75 |
|  |  | MBC6d | 2.5 | 4.0 | 0.2 | 2.0 | 0.06 | 0.50 | 0.56 |
|  |  |  | 2.5 | 4.0 | 0.6 | 1.0 | 0.25 | 0.25 | 0.50 |
|  |  |  | 2.5 | 4.0 | 1.3 | 0.1 | 0.50 | 0.03 | 0.53 |
| P.sp | TSB | MIC | 8.0 | 16.0 | 2.0 | 8.0 | 0.25 | 0.50 | 0.75 |
|  |  |  | 8.0 | 16.0 | 4.0 | 4.0 | 0.50 | 0.25 | 0.75 |
|  |  | MBC2d | 31.0 | 16.0 | 8.0 | 8.0 | 0.26 | 0.50 | 0.76 |
|  |  |  | 31.0 | 16.0 | 16.0 | 2.0 | 0.52 | 0.13 | 0.64 |

TABLE 9-continued

Combination of Compound A and p-Tolyldiiodomethylsulfone (Compound B)

| Microbe | Media | Test | end point activity in ppm | | | | calculations | | |
|---|---|---|---|---|---|---|---|---|---|
| | | | QA | QB | Qa | Qb | Qa/QA | Qb/QB | SI |
| | | MBC6d | 31.0 | 16.0 | 8.0 | 8.0 | 0.26 | 0.50 | 0.76 |
| | | | 31.0 | 16.0 | 16.0 | 2.0 | 0.52 | 0.13 | 0.64 |
| Ecol | M9G | MBC2d | 2.5 | 25.0 | 1.3 | 3.1 | 0.50 | 0.12 | 0.62 |
| | | | 2.5 | 25.0 | 0.6 | 6.2 | 0.25 | 0.25 | 0.50 |
| | | | 2.5 | 25.0 | 0.2 | 12.5 | 0.06 | 0.50 | 0.56 |
| Mixed | TSB | MIC | 3.1 | 50.0 | 0.3 | 6.2 | 0.10 | 0.12 | 0.22 |
| | | MBC4d | 3.1 | 100.0 | 0.6 | 12.5 | 0.20 | 0.13 | 0.33 |

The synergistic ratios of compound A:compound B range from 20:1 to 1:50. The preferred ratios are 8:1 to 1:20.

TABLE 10

Combination of Compound A and 3-Iodo-2-propynylbutylcarbamate (Compound B)

| Microbe | Media | Test | end point activity in ppm | | | | calculations | | |
|---|---|---|---|---|---|---|---|---|---|
| | | | QA | QB | Qa | Qb | Qa/QA | Qb/QB | SI |
| Ecol | TSB | MIC | 5.0 | 250.0 | 0.6 | 125.0 | 0.12 | 0.50 | 0.62 |
| | | | 5.0 | 250.0 | 1.3 | 31.0 | 0.25 | 0.12 | 0.37 |
| | | | 5.0 | 250.0 | 2.5 | 0.5 | 0.50 | 0.00 | 0.50 |
| | | MBC2d | 5.0 | 250.0 | 0.6 | 125.0 | 0.12 | 0.50 | 0.62 |
| | | | 5.0 | 250.0 | 1.3 | 31.0 | 0.25 | 0.12 | 0.37 |
| | | | 5.0 | 250.0 | 2.5 | 16.0 | 0.50 | 0.06 | 0.56 |
| | | MBC6d | 5.0 | 250.0 | 0.6 | 125.0 | 0.12 | 0.50 | 0.62 |
| | | | 5.0 | 250.0 | 1.3 | 31.0 | 0.25 | 0.12 | 0.37 |
| | | | 5.0 | 250.0 | 2.5 | 2.0 | 0.50 | 0.01 | 0.51 |
| Calb | TSB | MIC | 1.3 | 8.0 | 0.3 | 2.0 | 0.25 | 0.25 | 0.50 |
| | | | 1.3 | 8.0 | 0.6 | 1.0 | 0.50 | 0.13 | 0.62 |
| | | MBC2d | 1.3 | 8.0 | 0.3 | 4.0 | 0.25 | 0.50 | 0.75 |
| | | | 1.3 | 8.0 | 0.6 | 2.0 | 0.50 | 0.25 | 0.75 |
| | | MBC6d | 2.5 | 8.0 | 0.3 | 4.0 | 0.12 | 0.50 | 0.62 |
| | | | 2.5 | 8.0 | 0.6 | 2.0 | 0.25 | 0.25 | 0.50 |
| | | | 2.5 | 8.0 | 1.3 | 0.3 | 0.50 | 0.03 | 0.53 |
| P.sp | TSB | MIC | 8.0 | 125.0 | 2.0 | 62.0 | 0.25 | 0.50 | 0.75 |
| | | | 8.0 | 125.0 | 4.0 | 31.0 | 0.50 | 0.25 | 0.75 |
| | | MBC2d | 31.0 | 250.0 | 2.0 | 62.0 | 0.06 | 0.25 | 0.31 |
| | | | 31.0 | 250.0 | 4.0 | 31.0 | 0.13 | 0.12 | 0.25 |
| | | | 31.0 | 250.0 | 16.0 | 16.0 | 0.52 | 0.05 | 0.58 |
| | | MBC6d | 31.0 | 250.0 | 1.0 | 125.0 | 0.03 | 0.50 | 0.53 |
| | | | 31.0 | 250.0 | 4.0 | 62.0 | 0.13 | 0.25 | 0.38 |
| Ecol | M9G | MBC2d | 1.3 | 25.0 | 0.6 | 3.1 | 0.50 | 0.12 | 0.62 |
| | | | 1.3 | 25.0 | 0.2 | 12.5 | 0.13 | 0.50 | 0.63 |
| Mixed | TSB | MIC | 3.1 | 200.0 | 0.6 | 12.5 | 0.20 | 0.06 | 0.26 |
| | | MBC1d | 25.0 | 400.0 | 2.5 | 50.0 | 0.10 | 0.13 | 0.23 |
| | | MBC4d | 3.1 | 200.0 | 0.6 | 12.5 | 0.20 | 0.06 | 0.26 |

The synergistic ratios of compound A:compound B range from 5:1 to 1:200. The preferred ratios are 1:1 to 1:25.

TABLE 11

Combination of Compound A and Bis-(2-hydroxy-5-chlorophenyl)-methylene (Compound B)

| Microbe | Media | Test | end point activity in ppm | | | | calculations | | |
|---|---|---|---|---|---|---|---|---|---|
| | | | QA | QB | Qa | Qb | Qa/QA | Qb/QB | SI |
| Ecol | TSB | MIC | 2.5 | 62.0 | 0.6 | 31.0 | 0.25 | 0.50 | 0.75 |
| | | | 2.5 | 62.0 | 1.3 | 16.0 | 0.50 | 0.26 | 0.76 |
| | | MBC2d | 5.0 | 62.0 | 0.6 | 31.0 | 0.12 | 0.50 | 0.62 |
| | | | 5.0 | 62.0 | 1.3 | 16.0 | 0.25 | 0.26 | 0.51 |
| | | | 5.0 | 62.0 | 2.5 | 4.0 | 0.50 | 0.06 | 0.56 |
| | | MBC6d | 5.0 | 62.0 | 0.6 | 31.0 | 0.12 | 0.50 | 0.62 |
| | | | 5.0 | 62.0 | 1.3 | 16.0 | 0.25 | 0.26 | 0.51 |
| | | | 5.0 | 62.0 | 2.5 | 2.0 | 0.50 | 0.03 | 0.53 |
| Calb | TSB | MIC | 2.5 | 8.0 | 1.3 | 4.0 | 0.50 | 0.50 | 1.00 |
| | | MBC6d | 2.5 | 16.0 | 1.3 | 4.0 | 0.50 | 0.25 | 0.75 |
| P.sp | TSB | MIC | 16.0 | 62.0 | 2.0 | 31.0 | 0.13 | 0.50 | 0.63 |
| | | | 16.0 | 62.0 | 4.0 | 16.0 | 0.25 | 0.26 | 0.51 |
| | | | 16.0 | 62.0 | 8.0 | 2.0 | 0.50 | 0.03 | 0.53 |
| | | MBC2d | 31.0 | 250.0 | 2.0 | 125.0 | 0.06 | 0.50 | 0.56 |
| | | | 31.0 | 250.0 | 4.0 | 16.0 | 0.13 | 0.06 | 0.19 |
| | | | 31.0 | 250.0 | 8.0 | 31.0 | 0.26 | 0.12 | 0.38 |
| | | | 31.0 | 250.0 | 16.0 | 8.0 | 0.52 | 0.03 | 0.55 |
| | | MBC | 31.0 | 250.0 | 1.0 | 125.0 | 0.03 | 0.50 | 0.53 |
| | | | 31.0 | 250.0 | 4.0 | 62.0 | 0.13 | 0.25 | 0.38 |

TABLE 11-continued

Combination of Compound A and Bis-(2-hydroxy-5-chlorophenyl)-methylene (Compound B)

| Microbe | Media | Test | end point activity in ppm | | | | calculations | | |
|---|---|---|---|---|---|---|---|---|---|
| | | | QA | QB | Qa | Qb | Qa/QA | Qb/QB | SI |
| | | | 31.0 | 250.0 | 8.0 | 31.0 | 0.26 | 0.12 | 0.38 |
| | | | 31.0 | 250.0 | 16.0 | 8.0 | 0.52 | 0.03 | 0.55 |
| Ecol | M9G | MIC | 0.3 | 62.0 | 0.1 | 31.0 | 0.16 | 0.50 | 0.66 |
| | | MBCld | 0.3 | 62.0 | 0.1 | 31.0 | 0.16 | 0.50 | 0.66 |
| Mixed | TSB | MIC | 3.1 | 125.0 | 0.3 | 16.0 | 0.10 | 0.13 | 0.23 |
| | | MBCld | 25.0 | 125.0 | 0.6 | 31.0 | 0.02 | 0.25 | 0.27 |
| | | MBC4d | 3.1 | 125.0 | 0.3 | 16.0 | 0.10 | 0.13 | 0.23 |

The snyergistic ratios of compound A:compound B range from 4:1 to 1:800. The preferred ratios are 2:1 to 1:50.

TABLE 12

Combination of Compound A and Dipropylamine ether (Compound B)

| Microbe | Media | Test | end point activity in ppm | | | | calculations | | |
|---|---|---|---|---|---|---|---|---|---|
| | | | Qa | QB | Qa | Qb | Qa/QA | Qb/QB | SI |
| Ecol | M9G | MIC | 0.3 | 16.0 | 0.1 | 4.0 | 0.16 | 0.25 | 0.41 |
| | | | 0.3 | 16.0 | 0.1 | 0.5 | 0.26 | 0.03 | 0.29 |
| | | MBCld | 2.5 | 62.0 | 0.1 | 2.0 | 0.03 | 0.03 | 0.06 |
| | | MBC4d | 0.3 | 31.0 | 0.1 | 8.0 | 0.16 | 0.26 | 0.42 |
| | | MBC7d | 0.3 | 31.0 | 0.1 | 4.0 | 0.16 | 0.13 | 0.29 |
| Calb | TSB | MIC | 2.5 | 62.0 | 0.6 | 31.0 | 0.25 | 0.50 | 0.75 |
| | | | 2.5 | 62.0 | 1.3 | 8.0 | 0.50 | 0.13 | 0.63 |
| Ecol | TSB | MIC | 1.3 | 62.0 | 0.1 | 16.0 | 0.06 | 0.26 | 0.32 |
| | | MBCld | 1.3 | 62.0 | 0.3 | 31.0 | 0.25 | 0.50 | 0.75 |
| Mixed | TSB | MIC | 3.1 | 200.0 | 0.6 | 31.0 | 0.20 | 0.16 | 0.36 |
| | | MBC4d | 3.1 | 200.0 | 1.3 | 62.0 | 0.40 | 0.31 | 0.71 |

The synergistic ratios of compound A:compound B range from 1:6.2 to 1:200. The preferred ratios are 1:6.2 to 1:50.

TABLE 13

Combination of Compound A and Dodecylamine (Compound B)

| Microbe | Media | Test | end point activity in ppm | | | | calculations | | |
|---|---|---|---|---|---|---|---|---|---|
| | | | Qa | QB | Qa | Qb | Qa/QA | Qb/QB | SI |
| Calb | TSB | MIC | 2.5 | 25.0 | 1.3 | 0.4 | 0.50 | 0.02 | 0.52 |
| | | | 2.5 | 25.0 | 0.6 | 6.2 | 0.25 | 0.25 | 0.50 |
| | | | 2.5 | 25.0 | 0.3 | 12.5 | 0.12 | 0.50 | 0.62 |
| | | MBC2d | 2.5 | 50.0 | 1.3 | 1.6 | 0.50 | 0.03 | 0.53 |
| | | | 2.5 | 50.0 | 0.6 | 12.5 | 0.25 | 0.25 | 0.50 |
| | | | 2.5 | 50.0 | 0.3 | 25.0 | 0.12 | 0.50 | 0.62 |
| Ecol | M9G | MIC | 0.6 | 25.0 | 0.3 | 1.6 | 0.50 | 0.06 | 0.56 |
| | | | 0.6 | 25.0 | 0.1 | 12.5 | 0.13 | 0.50 | 0.63 |
| | | MBC2d | 1.3 | 25.0 | 0.6 | 1.6 | 0.50 | 0.06 | 0.56 |
| | | | 1.3 | 25.0 | 0.3 | 3.1 | 0.25 | 0.12 | 0.37 |

The synergistic ratios of compound A:compound B range from 2.5:1 to 1:160. The preferred ratios are 1:2.5 to 1:20.

TABLE 14

Combination of Compound A and 1-(3-chloroallyl)-3,5,7-triaza-1-azoniaadamantane chloride (Compound B)

| Microbe | Media | Test | end point activity in ppm | | | | calculations | | |
|---|---|---|---|---|---|---|---|---|---|
| | | | QA | QB | Qa | Qb | Qa/QA | Qb/QB | SI |
| Ecol | M9G | MIC | 0.3 | 31.0 | 0.04 | 8.0 | 0.13 | 0.26 | 0.39 |
| | | | 0.3 | 31.0 | 0.16 | 1.0 | 0.52 | 0.03 | 0.55 |
| | | MBC4d | 0.3 | 31.0 | 0.04 | 16.0 | 0.13 | 0.52 | 0.65 |
| | | | 0.3 | 31.0 | 0.08 | 2.0 | 0.26 | 0.06 | 0.32 |
| | | | 0.3 | 31.0 | 0.16 | 1.0 | 0.52 | 0.03 | 0.55 |
| | | MBC7d | 0.3 | 31.0 | 0.04 | 16.0 | 0.13 | 0.52 | 0.65 |
| | | | 0.3 | 31.0 | 0.08 | 2.0 | 0.26 | 0.06 | 0.32 |
| | | | 0.3 | 31.0 | 0.16 | 1.0 | 0.52 | 0.03 | 0.55 |
| Calb | TSB | MIC | 2.5 | 500.0 | 1.25 | 16.0 | 0.50 | 0.03 | 0.53 |
| Mixed | TSB | MIC | 3.1 | 1000.0 | 0.62 | 125.0 | 0.20 | 0.13 | 0.33 |
| | | MBC4d | 3.1 | 1000.0 | 0.62 | 125.0 | 0.20 | 0.13 | 0.33 |

The synergistic ratios of compound A:compound B range from 1:6.2 to 1:400. The preferred ratios are 1:6.2 to 1:200.

TABLE 15

Combination of Compound A and 2,4-dichlorobenzyl alcohol (Compound B)

| Microbe | Media | Test | end point activity in ppm | | | | calculations | | |
|---|---|---|---|---|---|---|---|---|---|
| | | | Qa | QB | Qa | Qb | Qa/QA | Qb/QB | SI |
| Ecol | TSB | MIC | 0.31 | 500.0 | 0.31 | 500.0 | NA | NA | NA |
| | | | | | 0.31 | 250.0 | NA | NA | NA |
| | | | | | 0.31 | 125.0 | NA | NA | NA |
| | | | | | 0.31 | 62.0 | NA | NA | NA |
| | | | | | 0.31 | 31.0 | NA | NA | NA |
| | | | | | 0.31 | 0.0 | NA | NA | NA |
| | | | | | 5.0 | 500.0 | NA | NA | NA |
| | | | | | 2.5 | 500.0 | NA | NA | NA |
| | | | | | 1.25 | 500.0 | NA | NA | NA |
| | | | | | 0.62 | 500.0 | NA | NA | NA |
| | | | | | 0.16 | 500.0 | NA | NA | NA |
| | | | | | 0.08 | 500.0 | NA | NA | NA |
| | | | | | 0.00 | 500.0 | NA | NA | NA |
| Ecol | M9G | MIC | 0.31 | 500.0 | 0.31 | 500.0 | NA | NA | NA |
| | | | | | 0.31 | 250.0 | NA | NA | NA |
| | | | | | 0.31 | 125.0 | NA | NA | NA |
| | | | | | 0.31 | 62.0 | NA | NA | NA |
| | | | | | 0.31 | 31.0 | NA | NA | NA |
| | | | | | 0.31 | 0.0 | NA | NA | NA |
| | | | | | 5.0 | 500.0 | NA | NA | NA |
| | | | | | 2.5 | 500.0 | NA | NA | NA |
| | | | | | 1.25 | 500.0 | NA | NA | NA |
| | | | | | 0.62 | 500.0 | NA | NA | NA |
| | | | | | 0.16 | 500.0 | NA | NA | NA |
| | | | | | 0.08 | 500.0 | NA | NA | NA |
| | | | | | 0.00 | 500.0 | NA | NA | NA |

NA = not applicable because they are not end-point activities.

TABLE 16

Combination of Compound A and 3,5-dimethyltetrahydro-1,3,5-(2H)-thiadizine-2-thione (Compound B)

| Microbe | Media | Test | end point activity in ppm | | | | calculations | | |
|---|---|---|---|---|---|---|---|---|---|
| | | | Qa | QB | Qa | Qb | Qa/QA | Qb/QB | SI |
| Ecol | TSB | MIC | 0.62 | 125.0 | 5.0 | 31.0 | 8.00 | 0.25 | 8.25 |
| | | | 0.62 | 125.0 | 2.5 | 62.0 | 4.00 | 0.50 | 4.50 |
| | | MBCld | 0.62 | 125.0 | 5.0 | 31.0 | 8.00 | 0.25 | 8.25 |
| | | | 0.62 | 125.0 | 2.5 | 62.0 | 4.00 | 0.50 | 4.50 |
| Ecol | M9G | MIC | 0.16 | 62.0 | 0.31 | 4.0 | 2.00 | 0.08 | 2.06 |
| | | | 0.16 | 62.0 | 0.62 | 8.0 | 4.00 | 0.12 | 4.12 |
| | | | 0.16 | 62.0 | 1.25 | 16.0 | 8.00 | 0.25 | 8.25 |
| | | MBCld | 0.16 | 62.0 | 0.31 | 8.0 | 2.00 | 0.06 | 2.06 |
| | | | 0.16 | 62.0 | 0.62 | 4.0 | 4.00 | 0.12 | 4.12 |
| | | | 0.16 | 62.0 | 1.25 | 16.0 | 8.00 | 0.25 | 8.25 |

As can readily be seen by inspection of Table 1 through Table 14, the combinations demonstrate synergistic antimicrobial activities as measured by minimum inhibitory concentrations (MIC) and synergistic biocidal activity as measured by minimum biocidal concentrations (MBC), and show surprisingly greater activity than the algebraic sum of the individual ingredients which make up the respective composition.

The synergistic activities in most cases are applicable to bacteria, fungi, and a mixture of bacteria and fungi. Thus, the combinations not only lower the use-level of biocide but also broaden the spectrum of activity. This is especially useful in situations where Compound A does not achieve the best results due to weak activity against certain organisms. A number of examples, as shown in Tables 1, 2, 3, 5, 9, 10 and 11 demonstrate the advantages of using a synergistic combination for the control of a less sensitive pseudomonad.

Two examples of non-synergistic combinations of Compound A with 2,4-dichlorobenzylalcohol and Compound A with 3,5-dimethyltetrahydro-1,3,5-(2H)-thiadiazine-2-thione are demonstrated in Table 15 and Table 16, respectively. Table 15 is an example of no effect by the combination of two compounds. The activity of Compound A (MIC=0.31 ppm) was not affected by the absence or presence up to 500 ppm of 2,4-dichlorobenzylalcohol. The activity of 2,4-dichlorobenzylalcohol (MIC=500 ppm) was not affected by Compound A from 0 to 5 ppm. Thus, no increase or decrease of activity can be attributed by the combination. Table 16 is an example of antagonistic effect by the combination of Compound A and 3,5-dimethyltetrahydro-1,3,5-(2H)-thiadiazine-2-thione because there was a loss of activity of Compound A due to the presence of 3,5-dimethyltetrahydro-1,3,5-(2H)-thiadiazine-2-thione in the combination.

It is apparent that many modifications and improvements may be made without departure from the scope of the invention which is not to be limited as recited in the appended claims.

What is claimed is:

1. A microbicidal composition comprising a synergistic mixture the first component of which is a 3:1 ratio of 5-chloro-2-methyl-4-isothiazolin-3-one and 2-methyl-4-isothiazolin-3-one and the second component of which is 5-bromo-5-nitro-1,3-dioxane wherein the ratio of first component to second component is in the range of from about 6.5:1 to 1:250.

2. The composition of claim 1, wherein the ratio of the first component to the second component, 5-bromo-5-nitro-1,3-dioxane, is in the range of from 6.5:1 to 1:125.

3. A method for inhibiting the growth of a member selected from the group consisting of bacteria, fungi, algae and mixtures thereof, in a locus subject to contamination by said members, which comprises incorporating onto or into the locus, in an amount which is effective to adversely affect the growth of said member, the composition of claim 1.

4. The method of claim 3 wherein the locus in an aqueous medium.

5. The method of claim 4 wherein the composition is between from about 5 to about 100 ppm.

* * * * *

UNITED STATES PATENT AND TRADEMARK OFFICE
CERTIFICATE OF CORRECTION

PATENT NO. : 4,990,525            Page 1 of 3

DATED : February 5, 1991

INVENTOR(S) : Jemin C. Hsu

It is certified that error appears in the above-identified patent and that said Letters Patent is hereby corrected as shown below:

Column 5;    Table 2, please correct columns 5 and 7 as per the attached.

Column 9;    Table 8, line 3 of data, column 3, please insert --MBCID--.

UNITED STATES PATENT AND TRADEMARK OFFICE
CERTIFICATE OF CORRECTION

PATENT NO. : 4,990,525

DATED : February 5, 1991

INVENTOR(S) : Jemin C. Hsu

It is certified that error appears in the above-identified patent and that said Letters Patent is hereby corrected as shown below:

On page 5 (Table 2), delete columns 5 and 7 and replace with the following:

| $Q_B$ | $Q_b$ |
|---|---|
| 25.0 | 12.5 |
| 25.0 | 3.1 |
| 25.0 | 12.5 |
| 25.0 | 6.2 |
| 25.0 | 0.8 |
| 25.0 | 12.5 |
| 25.0 | 6.2 |
| 50.0 | 25.0 |
| 50.0 | 6.2 |
| 50.0 | 25.0 |
| 50.0 | 6.2 |
| 50.0 | 0.2 |
| 50.0 | 25.0 |
| 50.0 | 12.5 |
| 100.0 | 50.0 |
| 100.0 | 12.5 |

UNITED STATES PATENT AND TRADEMARK OFFICE
CERTIFICATE OF CORRECTION

PATENT NO. : 4,990,525                               Page 3 of 3

DATED     : February 5, 1991

INVENTOR(S) : Jemin C. Hsu

It is certified that error appears in the above-identified patent and that said Letters Patent is hereby corrected as shown below:

| | |
|---|---|
| 100.0 | 50.0 |
| 100.0 | 25.0 |
| 6.2 | 1.6 |
| 6.2 | 3.1 |
| 6.2 | 1.6 |
| 6.2 | 3.1 |
| 12.5 | 1.6 |
| 25.0 | 6.2 |

Signed and Sealed this

Seventh Day of July, 1992

Attest:

DOUGLAS B. COMER

Attesting Officer  Acting Commissioner of Patents and Trademarks